(12) United States Patent
Calafiore et al.

(10) Patent No.: US 8,865,218 B2
(45) Date of Patent: Oct. 21, 2014

(54) MICROENCAPSULATION PROCESS OF SERTOLI CELLS, MICROCAPSULES OBTAINED AND USE FOR TREATMENT OF TYPE I DIABETES MELLITUS

(75) Inventors: Riccardo Calafiore, Ponte Rio Pg (IT); Giovanni Luca, Paola Cs (IT); Mario Calvitti, Perugia (IT); Ennio Becchetti, Perugia (IT); Paolo Puccetti, Perugia (IT); Francesca Fallarino, Perugia (IT); Claudio Nastruzzi, Pontegradella Fe (IT)

(73) Assignee: GH Care, Inc., Dix Hills, NY (US)

( * ) Notice: Subject to any disclaimer, the term of this patent is extended or adjusted under 35 U.S.C. 154(b) by 405 days.

(21) Appl. No.: 13/140,728

(22) PCT Filed: Dec. 18, 2009

(86) PCT No.: PCT/IB2009/055847
§ 371 (c)(1),
(2), (4) Date: Jun. 17, 2011

(87) PCT Pub. No.: WO2010/070618
PCT Pub. Date: Jun. 24, 2010

(65) Prior Publication Data
US 2011/0250280 A1 Oct. 13, 2011

(30) Foreign Application Priority Data

Dec. 19, 2008 (IT) .............................. RM2008A0686

(51) Int. Cl.
*A61K 9/50* (2006.01)
*A61K 35/48* (2006.01)

(52) U.S. Cl.
CPC ............... *A61K 9/5036* (2013.01); *A61K 35/48* (2013.01); *A61K 9/5089* (2013.01)
USPC .......................................... 424/493; 424/93.7

(58) Field of Classification Search
None
See application file for complete search history.

(56) References Cited

U.S. PATENT DOCUMENTS

| | | | |
|---|---|---|---|
| 4,956,128 A | 9/1990 | Hommel et al. | |
| 6,149,907 A | 11/2000 | Selawry | |
| 7,122,177 B2 * | 10/2006 | Elliott et al. | .................. 424/93.1 |

OTHER PUBLICATIONS

Luca, G., et al. "Encapsulation, In Vitro Characterization, and In Vitro Biocompatibility of Sertoli Cells in Alginate-Based Microcapsules" Tissue Engineering, vol. 13. Nov. 2007. pp. 641-649.
Luca, G., et al. "Improved Function of Rat Islets Upon Co-Microencapsulation With Sertoli's Cells in Alginate/Poly-L-Ornithine" AAPS PharmsciTech 2001, Article 15. Feb. 2001. pp. 1-7.
Luca, G., et al. "Le Cellule Del Sertoli Migliorano La Funzionalita Delle Insule Pancreatiche Di Ratto Adulto: Potenziali Applicazioni Nella Cura Radicale Del Diabete Mellito Di Tipo I Previa Co-Microincapsulazione In Microcapsule Di Alginato/Poli-L-Ornitina" Acta Technologiae et Legis Medicamenti, vol. 13, No. 1. Jan. 2002. pp. 61-71.
Vos, P., et al. "Upscaling the Production of Microencapsulated Pancreatic Islets" Biomaterials 1997, Vol. 18, No. 16. Feb. 1997. pp. 1085-1090.
International Search Report for PCT/IB2009/055847. Nov. 2010. (4 Pages).
Mazzitelli, et al., "Multicompartimental Microcapsules for Cell Entrapment", XVIth International Conference on Bioencapsulation, Dublin, Ireland, Sep. 4-6, 2008, pp. 1-4.
Nisco Engineering AG Encapsulation Unit—Var J30, Zurich Switzerland, Aug. 8, 2006, 1 page.
Suarez-Pinzon, et al., "Testicular Sertoli Cells Protect Islet B-Cells From Autoimmune Destruction in Nod Mice By A Transforming Growth Factor—B-1—Dependent Mechanism", Diabetes, vol. 49, Nov. 2000, pp. 1810-1818.
Thanos, et al., "Formulating the Alginate-Polyornithine Biocapsule For Prolonged Stability: Evaluation of Composition and Manufacturing Technique," Journal of Biomedical Materials Research Part A, vol. 83A, No. 1, Jan. 2007, pp. 216-224.
Walsh, et al., "Expression of Insulin By Sertoli Cells Reverses Diabetes in Scid Mice", Journal of Andrology, Suppl. S., Mar. 2008, p. 44.

\* cited by examiner

*Primary Examiner* — Allison Fox
(74) *Attorney, Agent, or Firm* — Tutunjian & Bitetto, P.C.

(57) ABSTRACT

The invention relates to the use of Sertoli cells (SC) microencapsulated into hydrogel-based microcapsules, for the prevention and/or treatment of Type 1 diabetes mellitus (T1DM) and to a process for producing microcapsules, preferably shaped as microspheres.

15 Claims, 5 Drawing Sheets

MICROENCAPSULATION PROCESS OF SERTOLI CELLS, MICROCAPSULES OBTAINED AND USE FOR TREATMENT OF TYPE I DIABETES MELLITUS

The invention relates to the use of Sertoli cells (SC) microencapsulated into hydrogel-based microcapsules, for the prevention and/or treatment of Type 1 diabetes mellitus (T1DM) and to a process for producing microcapsules, preferably shaped as microspheres. The product object of the invention is capable of inducing both the neogenesis of beta-cells, destroyed by the diabetic pathology, and the "cutting off" of the same autoimmune process responsible for such destruction in T1DM.

The treatment with microencapsulated SC allows preventing and treating T1DM without resorting to any transplantation of hexogen pancreatic islets (either human or animal). It should be noted that the product obtained from SC microencapsulation is fully comparable to a "conventional" drug.

STATE OF THE ART

The worldwide current incidence of type 1 diabetes mellitus (T1DM) is equal to about 30,000 new cases a year. At the basis of type 1 DM pathogenesis which mainly but non exclusively affects young people and teenagers, is the destruction of most insulin-producing pancreatic beta-cells by an autoimmune mechanism. In short, the organism loses the immune tolerance towards the pancreatic beta-cells in charge of insulin production and induces an immune response, mainly cell-mediated, associated to the production of autoantibodies, which leads to the self-destruction of beta-cells.

The current T1DM therapy, based on the administration of hexogen insulin, tends to restore the glucide homeostasis as close as possible to that observed in physiological conditions. Insulin therapy, however, is not capable of reproducing the pulsating rhythm of insulin secretion typical of normal beta-pancreatic cell in response to secretagogue stimuli.

The restoration of a physiological and steady endocrine-pancreatic function would therefore represent the final goal for the radical solution of the pathology. To this end, new strategies have been proposed, such as the transplantation of whole pancreas or that of islets isolated from pancreas of human donors.

The hexogen insulin therapy currently used does not represent in any way the final therapy for treating T1DM. To overcome this problem, approaches have long been proposed which envisage the transplantation of the entire pancreatic organ or that of islets separated from the pancreas of human or animal donors.

The transplantation of islets, compared to that of the whole pancreas, is less invasive but exhibits similar problems, and in particular:
1. Reduced availability of human pancreas from dead donors, and, as a consequence, of islets.
2. Need of subjecting the recipient to lifelong general pharmacological immunosuppression regimes. Such therapeutic option used to prevent the immune rejection of the transplanted tissue, however, is burdened by side effects that are still little known nowadays, but also potentially very serious.
3. Rejection of transplants of heterologous islets, since none of the immunosuppressive drugs currently used has proved capable of effectively preventing them.
4. Poor survival of the transplanted islet tissue over time.

The Sertoli cell (SC) has recently been revaluated in its functions and promoted from a mere structural support of the testicular seminiferous tubule to a real biochemical laboratory with countless trophic and immunological functions. In particular, it has been proved that SC cultures produce molecules that inhibit the proliferation of B and T lymphocytes (1). Moreover, to strengthen their immunoregulatory function, the SC can induce the apoptosis of T, B cells and natural killers, linking through their ligand FAS to the FAS expressed by the target cells (2).

Another mechanism through which the SC carry out their immunomodulating role is represented by the production of Transforming Growth Factor-$\beta$ (TGF-$\beta$) (3). This molecule affects the phenotype of differentiation of T CD4+ lymphocytes, favouring type Th2 (protective immunity) over type Th1 (non protective immunity). As a whole, the Sertoli activity may therefore have a direct clinical importance in T1DM, since beta cells are destroyed by an infiltrate mainly consisting of lymphocytes Th1 (INF-gamma positive).

The immunoregulating effect of SC, moreover, is associated to the production of several growth factors, differentiating and anti-apoptosis such as transforming growth factor (TGF-$\square$), Glial Derived Neuroprophic Factor (GDNF), interleukin-1 (IL-1), stem cell factor (cKit-ligand), Fas/Fas Ligand (Fas-L), activin A and finally BCL-w (4).

The closest prior art (bibliographic reference No. 5) describes the introduction of SC into ultrapure alginate microcapsules with the obtainment of microcapsules with a mean end diameter of 520±14 μm.

At the time of such article, at an international level, microcapsules were considered satisfactory with a diameter of about 500 μm and a percentage of "tails" not higher than 5%. Both the capsular diameter and the presence of tails are very important parameters. The first one, to be reduced as much as possible, to allow a more effective exchange of metabolites; the second one as it has recently been found that even a percentage of tails <5% could trigger important phlogosis due to the creation of "loci minoris resistentiae" wherein cellular antigens may be exposed.

The inventors of the present invention have surprisingly found a process that allows producing homogeneous microcapsules of smaller dimensions without the presence of tail structures that can encapsulate SC while keeping their vitality and functionality unaffected.

In consideration of the above, the invention proposes for the first time the possibility of preventing and/or treating T1DM by transplanting SC microencapsulated into hydrogel-based microspheres, without any presence of hexogen islet tissue.

The object of the present invention therefore is a process for the manufacture of hydrogel-based microcapsules, containing Sertoli cells (SC) according to claim 1.

BRIEF DESCRIPTION OF THE DRAWINGS

Nine figures are attached to the present description, which show.

DESCRIPTION OF THE INVENTION

In the first place, a homogeneous polysaccharide suspension of SC is produced: the solution has a 90% purity in terms of cellular composition and is obtained in a saline solution of ultrapure sodium alginate at a concentration comprised between 1 and 5% w/v, advantageously between 1 and 3%. The alginate used is ultrapure as it exhibits an endotoxin content not higher than 20 EU/g and a protein content <0.4%; air is advantageously used as fluid. SC are treated in advance with trypsin and EDTA (2 min), in order to obtain a homogeneous cellular suspension. The following were used to assess it:

immunocytochemistry techniques, incubating the preparation with anti-mullerian inhibiting factor (MIS) and fluorescin anti-vimentin antibodies, which respectively mark the MIS and vimentin molecules, both expressed by the SC only.

histochemical techniques to assess the presence of both alkaline phosphatase (colouring with Fast-Red) typical of peritubular cell, and of the 3-β-hydroxy-steroidodehydrogenase enzyme (colouring with Nitro-blue tetrazolium) which on the other hand is typical of Leydig cells.

The results obtained with such histochemical assays have allowed to prove the presence of 5-8% of peritubular and Leydig cells; these cellular populations, moreover, are useful (when present in these proportions) to ensure a molecular "cross-talk" favourable for the correct functionality of SC.

This suspension is aspired at a speed comprised between 10 and 60 ml/min producing a continuous flow of dimensionally homogeneous microdroplets through suction and extrusion using a fluid current, advantageously air, at controlled pressure. The suspension thus aspired is introduced in a needle-type element to be divided into highly homogeneous microdroplets. Advantageously, the needle-type element exhibits a buttonhole opening on the side surface thereof wherein a fluid current is introduced at a rate of 3-7 liters/min to obtain a continuous flow of homogeneous size microdroplets. The fluid current is obtained from a generator and before being used, it is subject to a pressure reduction to obtain a pressure drop in the flow—non flow transient not less than 0.3 Bar; to a regulation to obtain high reproducibility in the flow—non flow transient and linearity between number of revolutions and fluid current dispensed, and to a regulation and control of the output current between 0 and 10 NL/min.

The microdroplets may have a mean diameter comprised between 300 and 700 μm with a standard deviation below 40 μm. The microdroplets obtained are introduced in an aqueous solution, advantageously using sterilised water for injectable preparations, F.U, containing divalent cations or polycationic substances with resulting gelification and obtainment of said microcapsules.

A further object of the present invention are Sertoli cells as sole therapeutic agent for the prevention and radical cure of T1DM.

Advantageously, according to the process of the invention, the aspiration takes place continuously by a peristaltic pump at a flow speed comprised between 10 and 16 ml/min and said extrusion takes place through the "air monojet" system using a fluid flow, preferably air, comprised between 3 and 7 l/min. In the process, the exact calibration of said air flow, a characterising element of the entire method, is ensured by the below components of the system that are not present in previous methods (including that used in the "Closest Prior Art"). Before coming into contact with said suspension of said stage b) said air flow is subject to the following operations with the following devices:

the membrane pressure reducer Swagelok (KPR1JRF411A20000) which is capable of ensuring high reproducibility of the output pressure and so as to obtain a very low pressure drop in the flow/non flow transient below 0.3 Bar, serves for stabilising and making the air flow to be sent to the extruder reproducible;

regulation through a micrometric valve Swagelok (SS-SS6MM), in output to the pressure regulator, which allows regulating very finely the output air flow (0-10 NL/min) with a high reproducibility in the flow/non flow transient and maintaining linearity between number of revolutions and dispensed flow;

with rotating float flow meter (ROTAMETRO) Yokogawa, supplied by Precision Fluid (RAGK41-TOSS-SSNNN-M741A-TTCGN*A), located downstream of the micrometric valve, which allows a precise and quick reading of the output flow (0-10 NL/min) and thus the adjustment thereof through the micrometric valve.

A further object of the present invention are microcapsules containing SC obtainable according to the process of the invention, one of the features thereof is to exhibit the secretion of IGF-1 of microencapsulates SC identical to that of non-microencapsulates or "free" SC.

A further object of the present invention is the use of Sertoli cells, advantageously microencapsulated according to the process of the invention, as sole therapeutic agent for the production of a medicament of the prevention and radical cure of T1DM.

According to the invention, the microcapsules obtained can be subject to washing operations and/or further coating with natural and/or artificial polymers.

Compared to the prior art, the process of the invention allow a) producing microcapsules of smaller size, with fixed diameters (starting from 300 μm) and perfectly homogeneous, without the presence of "tails" structures and above all, without loss of vitality and functionality of the microencapsulated SC; b) increasing the number of microencapsulated SC by ml of alginate from $10^6$ SCs to $20^6$ SC by ml of alginate with imaginable implications on the possibility of implanting a larger number of SC in the smallest possible volume of polymer and c) increasing the functionality of microencapsulated SC, in particular relating to the production of IGF-1, the secretion thereof changes from 50 ng/ml/$20 \times 10^6$ cells) to 80 ng/ml/$20 \times 10^6$ cells substantially equal to that of "free" SC. With reference to the present invention, it should be noted that 1. For the first time, microencapsulated SC are proposed as final therapeutic approach, inducing the neogenesis of patient's beta-cell, destroyed by the autoimmune process.
2. An optimisation of the microencapsulation process has been obtained which leads to the production of microcapsules with improved features, such as the reduction of mean dimensions, the reduced polydispersity and the absence of morphological deformities of the microcapsules ("tails" and coalescences).

A further object of the present invention are compositions comprising SC contained in microcapsules obtainable by the process of the invention together with physiologically tolerable carriers to use for the prevention and treatment of T1DM. An example of carrier consists of saline for intraperitoneal administration.

Below are the detailed aspects of the present invention.
Purification of Polymers The polymers usable for microencapsulating the SC are not available on the market in the highly purified form strictly necessary for applications requiring parenteral administrations, such as human transplants. In these cases, in fact, strict internationally recognised criteria of "quality control" are required (see guidelines of the Ministry of Health and of U.S. Pharmacopeia).

Most commercial products, in fact, have quite high endotoxin levels (generally comprised between 30,000 and 60,000 EU/g) which make them totally unsuitable for transplant procedures, which require endotoxin levels not higher than 100 EU/g. As a consequence of the above, all the polymers used for producing microparticles are suitably subject to subsequent purification cycles that allow the drastic reduction of the endotoxins present.
Isolation of SC The SC may be isolated and purified from various animal sources, generally prepuberals. After anaesthesia, the animals are subject to bilateral orchiectomy. After the removal of the epididymis, the testicles are subject to multienzymatic digestion. Once the digestion is complete, the tubular tissue is subject to filtration. The tubules thus obtained are placed in a culture at 37° C. in a 5% atmosphere of CO2. After 48 hours in incubator, the SC start adhering to the culture plates, forming a cellular monolayer. The SC obtained are analysed in terms of purity, vitality and functionality. The cellular vitality test is routinely conducted immediately after the isolation, on the second day of culture and immediately before and after the microencapsulation process.

Production of Microencapsulated Sertoli Cells

The SC may be immobilised into microcapsules consisting of various hydrogels consisting of hydrophilic polymers used alone or in mixtures. The initial phase of the microencapsulation process envisages the obtainment of a continuous and calibrated flow of microdroplets. Various procedures may be used for obtaining the microdroplets: (a) "air-monojet" microencapsulator, (b) automatic vibrating encapsulator, (c) electrostatic microencapsulator e (d) microfluidic lab-on-a-chip systems.

Figure 3:
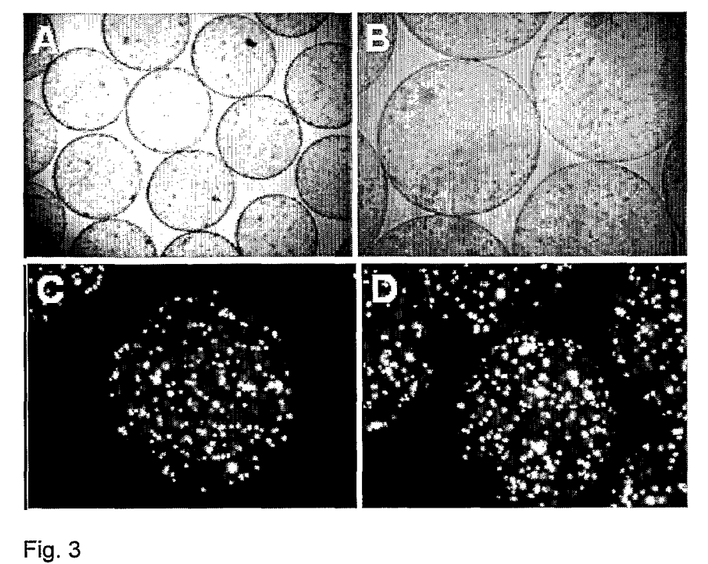
FIG. 3. Microphotographs of alginate-based microparticles obtained by the atomising system "air monojet", using $BaCl_2$ (A-C) and $CaCl_2$+polyornithine (B-D) as gelling agents.

Once a flow of microdroplets with controlled and homogeneous dimensions is obtained, these are transformed into solid microspheres through gelification procedures. For example: converging monolayers of SC are treated to obtain a homogeneous cellular suspension, the SC are resuspended in the various ultrapure polymeric solutions (obtained as described in section "Purification of polymers") and finally, the microcapsules obtained in the gelling bath are washed and isolated. The microcapsules produced may be used as such or be further coated with various natural, semi-synthetic or synthetic polymeric layers. The method proposed therefore allows (as shown by the pictures of FIG. 3) immobilising the SC into microcapsules with highly homogeneous dimensions, without morphological defects (presence of coalescences or "tail" structures), ensuring that the vitality and functionality features of the encapsulated cells are maintained.

In vivo Biocompatibility of Encapsulated SC

The microparticle biocompatibility is assessed through the intraperitoneal implant carried out through abdominal incision. The body weight of each recipient animal is monitored during all the in vivo study. At different times from the transplant, the microcapsules are explanted to assess their morphology and function of the encapsulated cells. The general features of the recovered microspheres were determined through microscopic analysis, assessing both the morphology and any presence of inflammatory cells of the capsule surface. The vitality of microencapsulated SC was also assessed using the dual colouring technique with EB/FDA.

Assessment of the In vivo Activity of Microencapsulated SC

It has been proved that the intraperitoneal transplant of microencapsulated SC in saline is capable of both preventing and treating T1DM in "stringent" animal models of human T1DM, such as NOD rats. Advantageously, but not exclusively, the administration of the product obtained from the microencapsulation of SC according to the invention takes place by intraperitoneal administration, with the product carried in saline.

Figure 9:
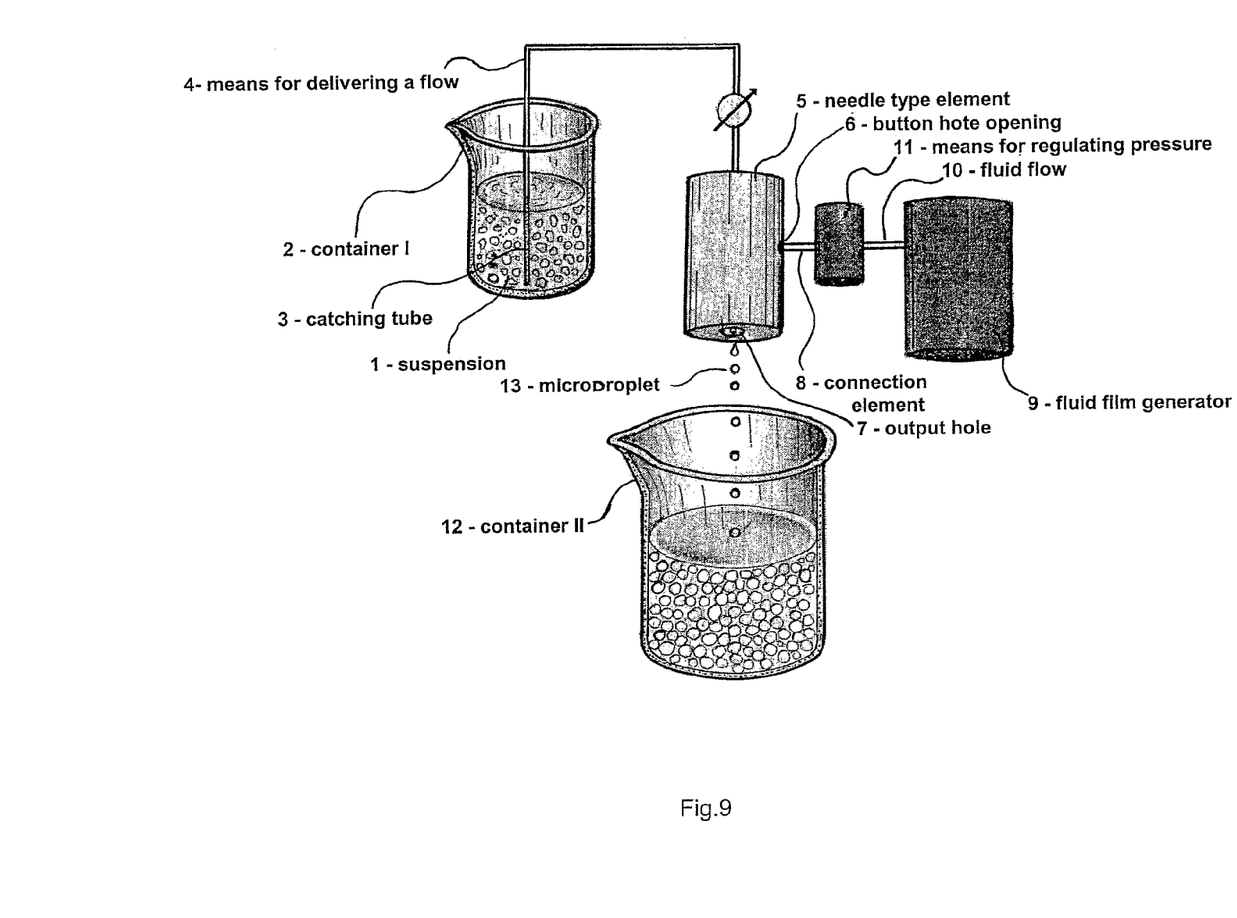
FIG. 9. Layout of the device according to the invention.

A further object of the invention is a device for producing microcapsules advantageously for applying the process of the invention. The device and the operation thereof shall now be described with reference to FIG. 9. A first container 2 cooperates with flow dispensing means 4, advantageously a volumetric pump, for delivering suspension 1 through the catching tube 3 to a needle-type element 5. The needle-type element 5 exhibits a buttonhole opening 6 in the lateral wall thereof and output hole 7. A joint 8 allows a pressure fluid current 10, preferably air, coming from a generator 9 and regulated by adjusting means 11, to enter inside element 5. By suitably regulating current 10 it is possible to interrupt the suspension flow and obtain microdroplets 13 of homogeneous size, which form gel in a solution containing divalent cations present in a second container 12. The airjet instrument mentioned above and the conditions described are applied for obtaining the homogeneous microcapsules.

Development of a prototype of microencapsulator usable in sterility conditions and GLP.

EXAMPLES

Microencapsulation of Sertoli cells into alginate-based microspheres and assessment of the in vivo biocompatibility and functionality.
Purification of the Polymer Sodium alginate obtained through a process of sequential filtrations, was used as base polymer for the production of microcapsules, usually available in a 1-6% (w/v) solution, appropriately stored in a place protected from light and at a temperature of 4°-6° C. Said compound is stable over time for about 5 years, has an endotoxin content not higher than 20 EU/g and a virtually absent protein content (<0.4%—another criterion of "bioinvisibility" of U.S. FDA).
Isolation of SC from Prepuberal Baby Swine The SC were isolated from testicles of baby swine (7-15 days old) "Large-White". After anaesthesia through the i.m. administration of 0.1 mg/kg azaperon (Stresnil® 40 mg/ml, Janssen, Brusselle, Belgium) and 15 mg/kg ketamine (Imalgene® 100 mg/ml, Gellini Farmaceutici, the swine were subject to bilateral orchiectomy. After the removal of the epididymis, the testicles are decorticated from the albuginea, finely chopped into small tissue fragments (1-3 mm3) and immediately subject to a first enzymatic digestion based on collagenase P (Roche Diagnostics, S.p.A., Monza, Italy) (2 mg/ml) in HBSS (Sigma Chemical Co, St. Louis, USA). The digestion is continued up to the separation of the seminiferous tubules. The collected tubules are then washed in HBSS and centrifuged at 500 r.p.m. After the wash, the tubules are incubated with a solution of HBSS containing trypsin (2 mg/ml) and DNAse I (Sigma). After the completion of the second digestion, the trypsin solution is diluted 1:1 with Hank's+20% FBS to stop the enzymatic activity thereof. After further washes with HBSS, the tubules are separated from the peritubular cells through a light centrifugation at 300 rpm. The "pellet" containing the tubular tissue is suitably filtered with a stainless steel filter with a 500 µm mesh opening. Finally, in order to remove any peritubular and Leydig cells contaminating the preparation, the suspension containing the tubules is further centrifuged at 800 rpm for 5 min and the resulting pellet is treated for 7 min with a glycine 1 M solution and EDTA 2 mM in HBSS at pH 7.2.

The tubules thus obtained are placed in a culture in HAM F12 (Euroclone) supplemented with retinoic acid 0.166 nM (Sigma) and with 5 ml/500 ml insulin-transferrin-selenium (ITS) (Becton Dickinson#354352), at 37° C. in a 5% atmosphere of CO2. After 48 hours of culture, the SC start adhering to the culture plates, forming a cellular monolayer. In order to remove the residual germ cells (which, as known, if implanted in the peritoneal cavity may give rise to dysgerminoms), the SC monolayers are treated with a buffer, tris-(hydroxymethyl)-aminomethane hydrochloride (TRIS) (Sigma) that allows eliminating the residual germ cells through osmotic lysis. Finally, the SC are grown in the above conditions, usually in 75 cm2 flasks.

Figure 1:
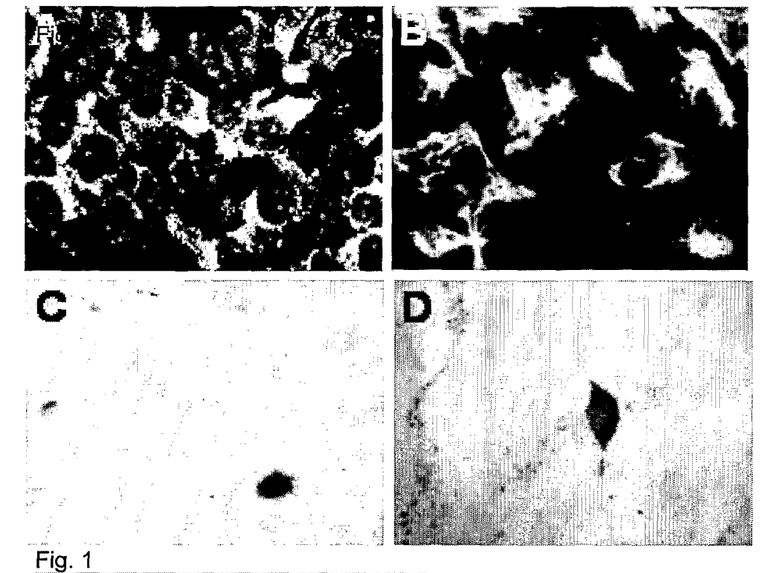
FIG. 1. Microphotographs of swine SC. A: Immunocytochemistry, obtained by incubating the preparation with anti-mullerian inhibiting factor (MIS) antibodies. B: Immunocytochemistry, obtained by incubating the preparation with anti-vimentin antibodies. C-D: To prove the poor presence of Leydig cells and peritubular cells, the preparation was subject to histochemical techniques to assess the presence of alkaline phosphatase, colouring with Fast-Red (typical of peritubular cells) (C), and of 3-$\beta$-hydroxy-steroidodehydrogenase activity, colouring with Nitro-blue tetrazolium (typical of Leydig) (D).

The SC obtained were analysed in terms of purity, vitality and functionality. The purity of the SC, which was higher than 90%, was assessed by immunocytochemistry techniques, incubating the preparation with anti-mullerian inhibiting factor (MIS) and fluorescin anti-vimentin antibodies, which respectively mark the MIS and vimentin molecules, both expressed by the SC only (FIG. 1A, B).

To prove the reduced presence of Leydig and peritubular cells as possible contaminants, the SC preparations were subject to histochemical assessments. These tests allow assessing both the presence of alkaline phosphatase (colouring with Fast-Red) typical of peritubular cell, and of the 3-β-hydroxy-steroidodehydrogenase enzyme (colouring with Nitro-blue tetrazolium) which on the other hand is typical of Leydig cells (FIG. 1C, D). The results obtained with these histochemical assays have allowed to prove the presence of 5-8% of peritubular and Leydig cells; these cellular populations, moreover, are useful (when present in these proportions) to ensure a molecular "cross-talk" favourable for the correct functionality of these populations of testicular cells.

The vitality of SC was determined by treatment with ethidium bromide (EB) and fluorescein-diacetate (FDA) (Sigma). The cells, observed by a fluorescence microscope, in all conditions showed a vitality higher than 95%. The cellular vitality test is routinely conducted immediately after the isolation, on the second day of culture and immediately before the microencapsulation process.
C) Production of Microdroplets for Encapsulating Sertoli Cells The SC were immobilised into microcapsules consisting of various polysaccharide polymers used alone or in mixtures. The selected polymer was sodium alginate ultrapurified at our laboratories. The initial phase of the microencapsulation process envisages the obtainment of a continuous and calibrated flow of microdroplets starting from cellular suspension of SC in an aqueous polysaccharide suspension with a polymeric concentration variable between 1 and 5% (w/v).

Various procedures were and may be used for obtaining the microdroplets: (a) "air-monojet" microencapsulator, (b) automatic vibrating encapsulator, (c) electrostatic microencapsulator e (d) microfluidic lab-on-a-chip systems.

In particular, the method selected (a), based on a semi-automatic, compact, sterilisable and transportable microencapsulator (FIG. 2, A shows an overall view of the system), has allowed producing microcapsules containing SC with highly homogeneous dimensions (300 to 700 µm diameter), without any evident morphological flaw (such as the presence of coalescences or "tail" structures) and above all, without the loss of vitality and functionality of the microencapsulated SC.

Figure 2:
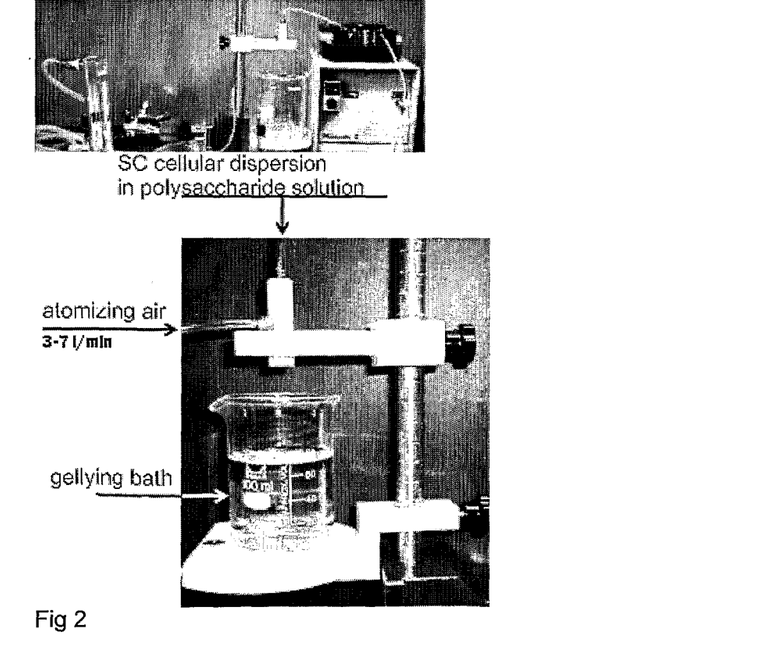
FIG. 2. Apparatus for the production of SC microencapsulated into alginate-based hydrogels through "air-monojet" (Panel A). Panel B shows the most important components of the devised system.

Panel B of FIG. 2 schematises the procedure of the microencapsulation process through "air-monojet".
D) Preparation of Ultrapurified Alginate-based Microcapsules Once a flow of microdroplets with controlled and homogeneous dimensions is obtained, these are transformed into solid microspheres through a gelification procedure which envisages the forming of ionic links with divalent ions according to a method developed and validated at our laboratories.

In particular, converging monolayers of SC are treated with 0.05% trypsin/EDTA (Gibco, Garndisland, USA) (2 min), in order to obtain a homogeneous cellular suspension. Once washed, the SC are counted by hemocytometric analysis and tested for vitality. Afterwards, the SC are resuspended in the various ultrapure polymeric suspensions in concentrations variable between 1.5-2% (w/v) of AG. For the production of microcapsules with the "air-monojet" system, the SC suspension in the polymers is continuously aspired by a peristaltic pump at a flow speed comprised between 10 and 16 ml/min. The cellular suspension is then extruded through the "air monojet" system (using an air flow comprised between 3 and 7 l/min). During the entire process, the SC suspension is kept under light stirring to prevent the cellular aggregation and the possible formation of microcapsules with non-homogeneous distribution of SC therein.

The microdroplets produced are gellied with a solution containing divalent cations, such as Ca+2 or Ba+2 (0.5-2.5%, w/v). In this way, the microdroplets are instantly transformed into gel microspheres. Afterwards, the microcapsules are left to settle for periods variable between 2 and 15 min into the gelling bath. At the end of this step, the microcapsules are subject to repeated washing cycles with saline.

The microcapsules produced may be used as such or be further coated through sequential incubation in solutions containing natural, semi-synthetic or synthetic cationic polymers. For example, poly-L-ornithine (PLO) was used at 0.12% (for 10 min) and at 0.06% (for 6 min). Finally, the microcapsules coated with PLO are further treated with a diluted solution of polysaccharide, to provide the highly biocompatible final outer coating.

FIG. 3 shows the microphotographs of alginate-based microcapsules obtained by the procedure described above, both using only Barium ions (A-C) and the procedure of the multiple coating with Calcium/polyornithine/polymer ions (B-D). The method proposed therefore allows (as shown by the pictures of FIG. 3) immobilising the SC into microcapsules with highly homogeneous dimensions, without morphological defects, such as the presence of coalescences or "tail" structures, and finally, ensuring that the vitality and functionality features of the encapsulated cells are maintained.

E) In vivo Biocompatibility of Encapsulated SC

After general anaesthesia, induced by intra-peritoneal administration of 100 mg/kg ketamine (Parke-Davis/Pfizer, Karlsruhe, Germany) and 15 mg/kg xylazine (Bayer, Leverkusen, Germany), the alginate microparticles were introduced through a small abdominal incision in the peritoneal cavity of female NOD rats (Harlan, Italy, approximate weight of 25 g). 106 microencapsulated SC were implanted in each animal. The body weight of each recipient rat was monitored during all the in vivo study.

After 4 months from the transplant, the microcapsules were explanted, after anaesthesia, from the peritoneal cavity of the animals to assess their morphology and function of the contents. The microcapsules were recovered by peritoneal wash using saline. The general features of the recovered microspheres were determined through microscopic analysis, assessing both the morphology and any presence of inflammatory cells of the capsule surface. The vitality of microencapsulated SC was also assessed using the dual colouring technique with EB/FDA.

Figure 4:
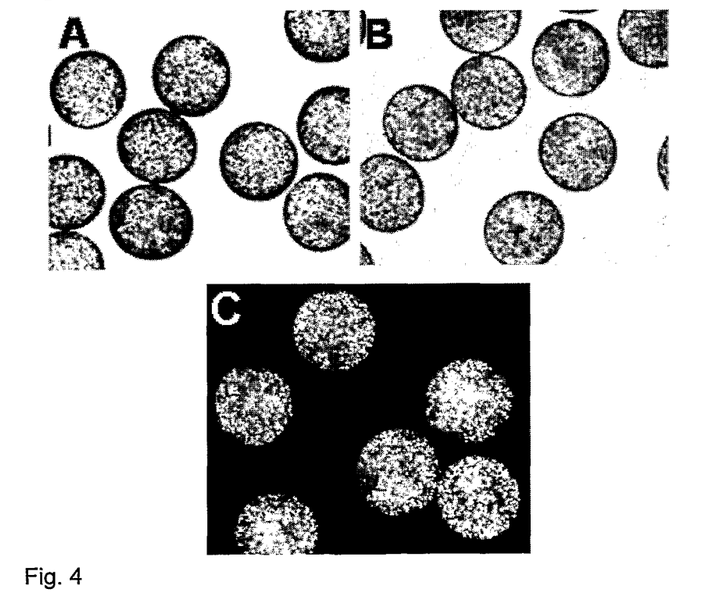
FIG. 4. Microphotographs in clear field of polysaccharidic microparticles cross-linked with Barium (A) and Calcium (B) ions after recovery from the peritoneal cavity of NOD rats 4 months after the implant. Panel C shows a microphotograph obtained by a fluorescence microscope of SC microencapsulated in barium alginate after a dual colouring with EB/FDA.

The microphotographs shown in FIG. 4 (A-B) show that the polysaccharidic microparticles keep high biocompatibility standards, as shown by the minimum levels of inflammatory cells present on the capsular surface. Moreover, the microencapsulated SC both in Barium (FIG. 4A) and calcium (FIG. 4B) alginate, keep excellent vitality levels 4 months after the implantation (FIG. 4C).

E) Assessment of the In vivo and In vitro Activity of Microencapsulated SC

The present invention finds application in the field of transplantation biotechnologies, such as for example the prevention and treatment of T1DM. Actually, at our laboratories we have proved that the intraperitoneal transplant of microencapsulated SC in barium alginate microspheres (206/rat) is capable of both preventing and treating T1DM in "stringent" animal models of human T1DM, such as NOD rats. In particular, SC microencapsulated into barium alginate (BaAG) microspheres were transplanted, after 72 hours culture, in the peritoneal cavity of pre-diabetic NOD rats and affected by evident diabetes. The implantation was carried out in a general anaesthesia through laparotomy. The transplanted animals were then monitored with weekly checks for their body weight and glycaemia before and after meals. The experimental protocol we followed envisaged groups of animals subject to different treatments as indicated below.

Group A: "naive" pre-diabetic control animals (treated with empty microcapsules).

Group B: control animals (treated with empty microcapsules) with spontaneous diabetes.

Group C: "naive" pre-diabetic animals treated with intraperitoneal implant of microencapsulated SC.

Group D: "naive" pre-diabetic animals treated with intraperitoneal implant of "free" SC: (206/rat).

Group E: animals with spontaneous diabetes treated with intraperitoneal implant of microencapsulated SC.

During the course of the in vivo study, some animals were sacrificed to assess the peripheral immunological layout through collection of spleen, peripancreatic lymph nodes and pancreas with concurrent histomorphological and immunocytochemical examinations.

The complete analysis of in vivo experiments on NOD rats has allowed proving that microencapsulated SC transplanted in pre-diabetic animals suffering from spontaneous diabetes allowed obtaining, important therapeutic results, as shown below.

Figure 5:
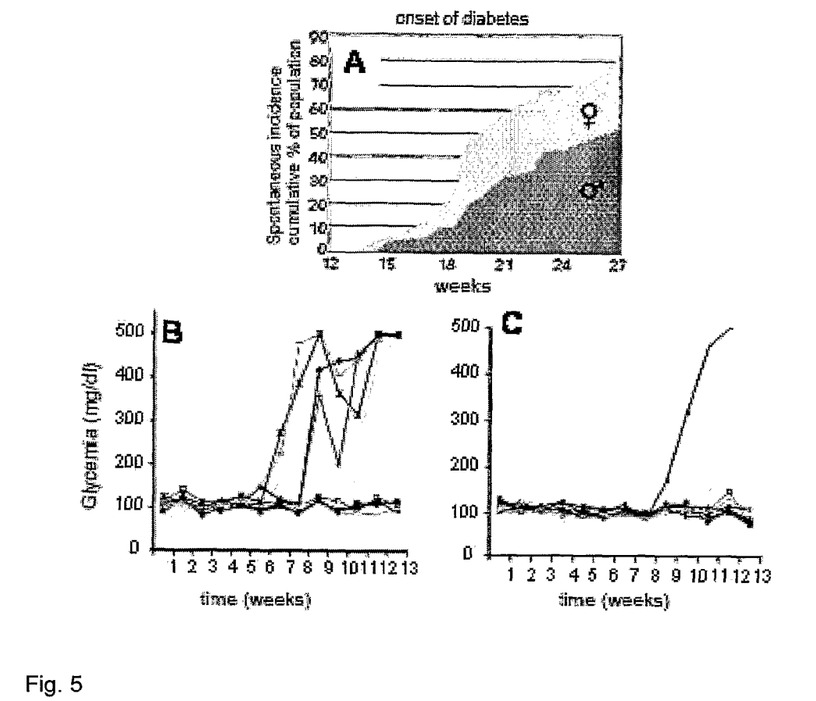
FIG. 5. Percentages of spontaneous onset of T1DM (85%) declared by the supplier of NOD rats (Taconic) (A), comparable to those shown by the pre-diabetic animals of the "naive" control group treated with empty microcapsules (B). On the other hand, panel C shows how the pre-diabetic animals treated with encapsulated SC have a percentage of onset of T1DM considerably reduced, equal to just 9% (preventive effect).

(A) Microencapsulated SC are capable of preventing the onset of T1DM in NOD rats. This sensational result can be obtained from the analysis of the percentages of spontaneous onset of T1DM. In fact, this pathology occurred spontaneously in 85% of the animals in group A (FIG. 5B). This result is perfectly in line with the percentages of occurrence of T1DM declared by the supplier of NOD rats (Taconic) (FIG. 5A). On the other hand, in the animals of group C (the pre-diabetic ones treated with encapsulated SC), the percentage of onset of T1DM was only 9% (FIG. 5C). Finally, in the animals of group D (pre-diabetic treated with intraperitoneal implant of "free" SC), the percentage of onset of T1DM was greatly reduced compared to that of the "naive" (19%), although higher than in the animals of group C (FIG. 5D).

Figure 6:
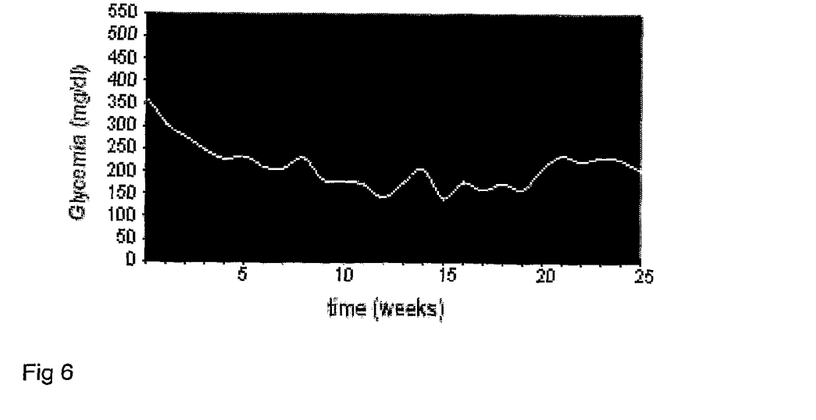
FIG. 6. Values of post-transplant mean glycaemia in NOD rats (Group E), with evident spontaneous diabetes treated with microencapsulated SC (therapeutic effect).

(B) The microencapsulated SC are capable of normalising, in just 7-15 days from the implant, the glycaemic values (with the attainment of glycaemia below 200 mg/dl) in more than 60% of rats in Group E (N=30) that had spontaneously developed diabetes (FIG. 6A). On the other hand, the animals in Group B (diabetics treated with empty capsules) always kept high levels of glycaemia, dying quickly, in 1-2 weeks. Finally, the animals in group F (N=30) (diabetics treated with intraperitoneal implant of "free" SC) were able to normalise the glycaemic values although in a lower percentage, equal to about 40%.

Figure 7:
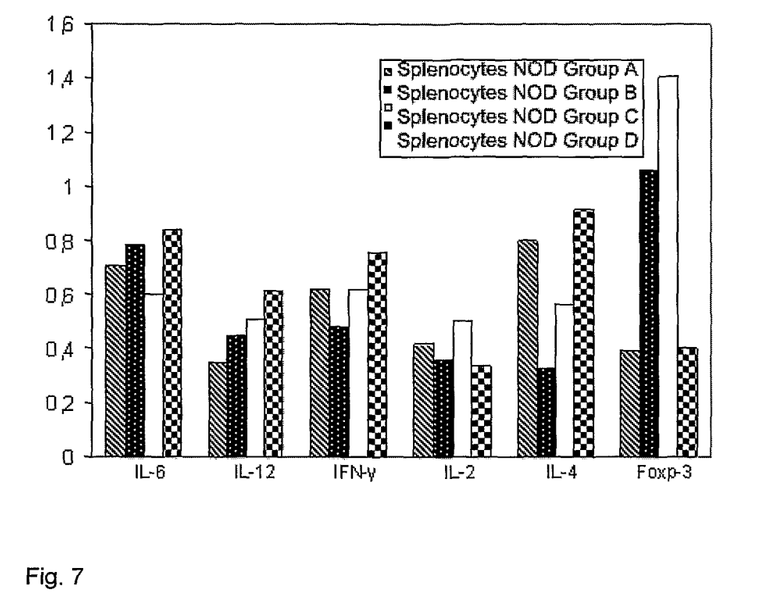
FIG. 7. Analysis RT-PCR on splenocytes of animals treated with microencapsulated SC. The results show that in animals from Groups C and E (see section VII), the treatment with SC can increase the number of positive in vivo Foxp3 cells. This result denotes an important increase of T cells with regulating features, that is, capable of regulating the activation and the proliferation of several cells involved in immune responses.

(C) Studies carried out on lymph nodes, pancreas and spleens have shown that the SC are capable of "re-educating" the immune system of the animals in Groups C and E, "blocking" the autoimmune attack responsible for the disease, as can be seen from FIG. 7 relating to real time Polymerase chain reaction (PCR) results on the splenocytes of treated animals. In particular, such results show that one of the main effects of the treatment with SC is their capacity to induce in vivo Foxp3+ cells. Foxp3 is a selective marker of T cells with regulating features, that is, capable of regulating the activation and the proliferation of several cells involved in immune responses and the number whereof is reduced in the NOD rat model.

Figure 8:
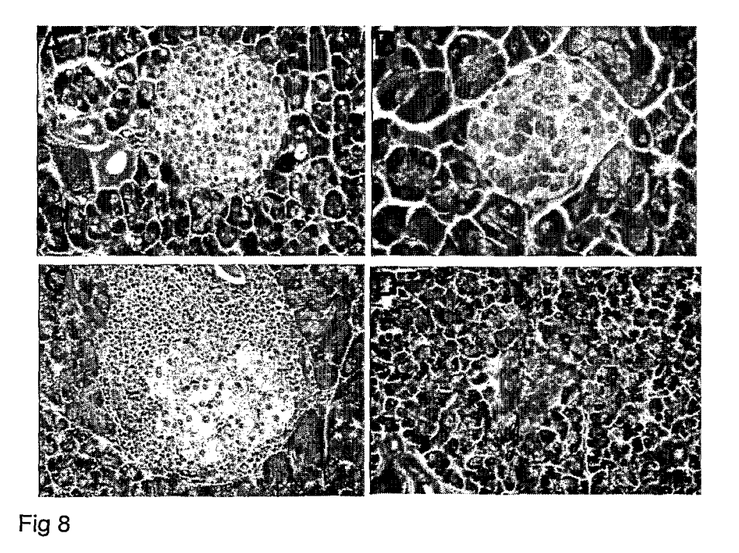
FIG. 8. Histological analysis of pancreatic islets of pre/diabetic NOD rats (A) and rats with spontaneous diabetes (B). The images show that the islet is totally free from both perk and intrainsular insulitic infiltrate. Panels C and D show the histological analyses of islets of pre-diabetic "naive" NOD rats (C) and suffering from spontaneous diabetes (D) treated with empty capsules.

(D) Histochemical assays carried out on all the groups of animals studied show that the treatment with SC is capable of removing the insulitic mononuclear infiltrate at the pancreas level in animals of groups C and E compared to those of the control groups (A and B) (FIG. 8). Moreover, such effect was followed by the activation of pancreatic mesenchymal stem cells capable of generating new β-cells which are capable of normalising glycaemia in animals treated with SC, as they are not undermined by the autoimmune attack anymore. The remodulation of the immune response after treatment with SC is mediated by the activation of the immunoregulatory pathway of the indoleamine 2 3-dioxygenase (IDO) enzyme, an isoform whereof is expressed and functioning in SC, too.

Bibliographic References
1. DeCesaris P, Filippini A, Cervelli C, Riccioloi, A.; Muci, S.; Starace, G.; Stefanini, M.; Ziparo, E. Immuno-suppressive molecules produced by Sertoli cells cultured in vitro: Biological effects on lymphocytes. Biochem. Biophys Res. Commun. 1992, 186: 1639-1646.
2. Lynch DH, Ramsdell F, Alderson MR. Fas and FasL in the homeostatic regulation of immune responses. Immunol. Today 1995, 16: 569-574.
3. Suarez-Pinzon W, Korbutt G S, Power R, Hooten J, Rajotte R V, Rabinovitch A. Testicular Sertoli cells protect islet B-cells from autoimmune destruction by a transforming growth factor-β1-dependent mechanism. Diabetes 2000, 49:1810-1818.
4. Emerich, D. F., Hemendinger, R., and Halberstadt, C. R. The Testicular-Derived Sertoli Cell: Cellular Immunoscience to Enable Transplantation. Cell Transplantation 12, 335, 2003.
5. Luca, G., Calvitti, M., Nastruzzi, C., Bilancetti, L., Becchetti, E, Mancuso, F., Calafiore R. Encapsulation, in Vitro Characterization and in Vivo Biocompatibility of Sertoli's Cells in Alginate Based Microcapsules. Tissue Eng. 2007, 13:641-648.

The invention claimed is:

1. A process for the manufacture of hydrogel-based microcapsules, containing Sertoli cells (SC), comprising the following steps:
   a. production of a homogeneous suspension of SC with purity, in terms of cell composition, higher than 90%, in a saline solution of ultrapure sodium alginate with a concentration ranging from 1 to 5% w/v;
   b. aspiration of said suspension at a speed between 10 and 60 ml/minute and introduction into a needle-type element;
   c. regulation of pressure in the needle-type element comprising:
   subjecting a fluid stream to a pressure reduction so as to obtain a constant pressure to stabilize an output fluid flow to the needle-type element, and
   regulating the output fluid flow to obtain a reproducibility in a transient stage;
   d. extrusion of said suspension inside said needle-type element through emission of a fluid stream of 3-7 liter/min thereby obtaining a continuous flow of microdroplets showing homogeneous dimensions; and
   e. introduction of said microdroplets of said flow into an aqueous solution containing divalent cations or polycationic substances with resulting gelification and obtainment of said microcapsules.

2. The process according to claim 1, wherein said needle-type element shows a buttonhole opening on its lateral wall and said fluid stream is inserted through said opening.

3. The process according to claim 1, wherein the microcapsules are made of sodium alginate, at a concentration of 1-3% w/v, with an endotoxin content not exceeding 20 EU/g and a protein content lower than 0.4%.

4. The process according to claim 1, wherein said fluid stream is obtained by a generator and before being used in said step d) further comprises:
   a. the pressure reduction obtains a pressure fall in the transient stage flux/no flux below 0.3 bar;
   b. regulation to obtain higher reproducibility in the transient stage flux/no flux and a linear correlation between numbers of routes and produced fluid stream; and
   c. regulation and tuning of the output fluid flow to between 0 and 10 NL/min.

5. The process according to claim 1, wherein said microcapsules obtained from step e) undergo washing and/or subsequent further coating with natural and/or artificial polymers.

6. The process according to claim 1, further comprising:
   treating a mammal with the microcapsules with SC as a sole therapeutic agent for the prevention and treatment of Type 1 diabetes mellitus (T1DM).

7. The process according to claim 6, wherein the microcapsules with SC each include at least $20 \times 10^6$ SC.

8. The process according to claim 6, wherein the needle-type element shows a buttonhole opening on its lateral wall and the fluid stream is inserted through the opening.

9. The process according to claim 6, wherein the microcapsules are made of sodium alginate, at a concentration of 1-3% w/v, with an endotoxin content not exceeding 20 EU/g and a protein content lower than 0.4%.

10. A process for the manufacture of hydrogel-based microcapsules, containing Sertoli cells (SC), comprising the following steps:
    producing a homogeneous suspension of SC with a higher than 90% purity, in terms of cell composition, in a saline solution of ultrapure sodium alginate;
    aspirating the suspension and introducing the suspension into a needle-type element;
    regulating pressure in the needle-type element comprising:
       subjecting a fluid stream to a pressure reduction so as to obtain a constant pressure to stabilize an output fluid flow to the needle-type element, and
       regulating the output fluid flow to obtain a reproducibility in a transient stage;
    extruding the suspension inside the needle-type element through emission of a fluid stream to obtain a continuous flow of microdroplets showing homogeneous dimensions; and
    introducing the microdroplets of the flow into an aqueous solution containing divalent cations or polycationic substances with resulting gelification and obtainment of the microcapsules.

11. The process according to claim 10, further comprising treating a mammal with the microcapsules with SC as a sole therapeutic agent for the prevention and treatment of Type 1 diabetes mellitus (T1DM).

12. Sertoli cell (SC) containing microcapsules obtainable according to a process for the manufacture of hydrogel-based microcapsules, containing Sertoli cells (SC), comprising the following steps:
    a. production of a homogeneous suspension of SC with purity, in terms of cell composition, higher than 90%, in a saline solution of ultrapure sodium alginate with a concentration ranging from 1 to 5% w/v;
    b. aspiration of said suspension at a speed between 10 and 60 ml/minute and introduction into a needle-type element;

c. regulation of pressure in the needle-type element comprising:

subjecting a fluid stream to a pressure reduction so as to obtain a constant pressure to stabilize an output fluid flow to the needle-type element, and regulating the output fluid flow to obtain a reproducibility in a transient stage;

d. extrusion of said suspension inside said needle-type element through emission of a fluid stream of 3-7 liter/min thereby obtaining a continuous flow of microdroplets showing homogeneous dimensions; and e. introduction of said microdroplets of said flow into an aqueous solution containing divalent cations or polycationic substances with resulting gelification and obtainment of said microcapsules.

13. The SC containing microcapsules according to claim 12 containing at least $20\times10^6$ SC.

14. The SC containing microcapsules according to claim 12 as a sole therapeutic agent for the prevention and treatment of Type 1 diabetes mellitus (T1DM).

15. Compositions comprising the SC containing microcapsules as claimed in claim 12 together with physiologically tolerable carriers for use in the prevention and treatment of Type 1 diabetes mellitus (T1DM).

* * * * *